US009176248B2

(12) United States Patent
L'Her et al.

(10) Patent No.: US 9,176,248 B2
(45) Date of Patent: Nov. 3, 2015

(54) METHOD FOR ESTIMATING AN UNDERWATER ACOUSTIC SOUND VELOCITY IN A NETWORK OF ACOUSTIC NODES, CORRESPONDING COMPUTER PROGRAM PRODUCT, STORAGE MEANS AND DEVICE

(75) Inventors: Christophe L'Her, Loperhet (FR); Dominique Barbot, Locmaria Plouzane (FR)

(73) Assignee: SERCEL, Carquefou (FR)

( * ) Notice: Subject to any disclaimer, the term of this patent is extended or adjusted under 35 U.S.C. 154(b) by 701 days.

(21) Appl. No.: 13/536,045

(22) Filed: Jun. 28, 2012

(65) Prior Publication Data

US 2013/0003498 A1    Jan. 3, 2013

(30) Foreign Application Priority Data

Jun. 29, 2011   (EP) .................................... 11305835

(51) Int. Cl.
*G01V 1/38*       (2006.01)
*G01N 29/024*     (2006.01)

(52) U.S. Cl.
CPC ................. *G01V 1/38* (2013.01); *G01N 29/024* (2013.01); *G01V 1/3817* (2013.01); *G01N 2291/011* (2013.01)

(58) Field of Classification Search
CPC ....... G01V 1/20; G01V 1/201; G01V 1/3835; G01V 1/38; G01N 29/024; G01N 2291/011
USPC .......................................................... 367/19
See application file for complete search history.

(56) References Cited

U.S. PATENT DOCUMENTS

| 3,174,128 | A |   | 3/1965  | Dow et al.       |         |
|-----------|---|---|---------|------------------|---------|
| 4,173,748 | A | * | 11/1979 | Lewandowski      | 367/123 |
| 4,187,492 | A | * | 2/1980  | Delignieres      | 367/127 |
| 4,912,682 | A | * | 3/1990  | Norton et al.    | 367/19  |
| 4,970,698 | A | * | 11/1990 | Dumestre, III    | 367/19  |
| 4,992,990 | A | * | 2/1991  | Langeland et al. | 367/19  |
| 5,031,159 | A | * | 7/1991  | Rouquette        | 367/125 |

(Continued)

FOREIGN PATENT DOCUMENTS

WO     2011014071 A2    2/2011

OTHER PUBLICATIONS

European Search Report and Written Opinion dated Nov. 25, 2011 for corresponding European Application No. 11305835.8, filed Jun. 29, 2011.

*Primary Examiner* — Ari M Diacou
(74) *Attorney, Agent, or Firm* — David D. Brush; Westman, Champlin & Koehler, P.A.

(57) ABSTRACT

A method for estimating an underwater acoustic sound velocity in a network of acoustic nodes arranged along towed acoustic linear antennas and in which a plurality of acoustic signals are transmitted between the nodes. The method includes: obtaining two predetermined distances each separating a couple of nodes placed along a same first acoustic linear antenna (31); for each couple of first and second nodes, obtaining a first propagation duration of an acoustic signal transmitted between said first node and a third node placed along a second acoustic linear antenna and a second propagation duration of an acoustic signal transmitted between said second node and said third node; and estimating said underwater acoustic sound velocity, as a function of said two predetermined distances and said first and second propagation durations obtained for each couple of nodes.

12 Claims, 4 Drawing Sheets

(56) References Cited

U.S. PATENT DOCUMENTS

| | | | |
|---|---|---|---|
| 5,668,775 A * | 9/1997 | Hatteland | 367/19 |
| 5,889,490 A * | 3/1999 | Wachter et al. | 342/127 |
| 6,697,300 B1 * | 2/2004 | Holt | 367/127 |
| 7,835,221 B2 * | 11/2010 | Vigen et al. | 367/19 |
| 7,944,774 B2 * | 5/2011 | Monk et al. | 367/21 |
| 8,385,152 B2 * | 2/2013 | Brumley | 367/89 |
| 8,867,305 B2 * | 10/2014 | Mellier et al. | 367/19 |
| 2004/0240317 A1 * | 12/2004 | Doisy et al. | 367/12 |
| 2005/0058022 A1 * | 3/2005 | Kitchin et al. | 367/130 |
| 2005/0180263 A1 * | 8/2005 | Lambert et al. | 367/128 |
| 2007/0091719 A1 * | 4/2007 | Falkenberg et al. | 367/19 |
| 2007/0230268 A1 * | 10/2007 | Hoogeveen et al. | 367/19 |
| 2008/0008031 A1 * | 1/2008 | Vigen et al. | 367/15 |
| 2008/0025146 A1 | 1/2008 | Welker | |
| 2008/0221449 A1 * | 9/2008 | Sato | 600/442 |
| 2009/0245019 A1 * | 10/2009 | Falkenberg et al. | 367/17 |
| 2012/0095629 A1 * | 4/2012 | Fjellstad et al. | 701/21 |
| 2013/0003503 A1 * | 1/2013 | L'Her et al. | 367/106 |

\* cited by examiner

METHOD FOR ESTIMATING AN UNDERWATER ACOUSTIC SOUND VELOCITY IN A NETWORK OF ACOUSTIC NODES, CORRESPONDING COMPUTER PROGRAM PRODUCT, STORAGE MEANS AND DEVICE

CROSS-REFERENCE TO RELATED APPLICATIONS

None.

STATEMENT REGARDING FEDERALLY SPONSORED RESEARCH OR DEVELOPMENT

None.

THE NAMES OF PARTIES TO A JOINT RESEARCH AGREEMENT

None.

FIELD OF THE DISCLOSURE

The disclosure relates to the field of geophysical data acquisition. More specifically, it relates to equipment for analyzing the geological layers underneath the sea bed. The disclosure relates in particular to the oil prospecting industry using seismic method, but can apply to any field using a system for acquiring geophysics data in a marine environment.

More specifically, the disclosure pertains to a technique for estimating an underwater acoustic sound velocity in a network of acoustic nodes arranged along towed acoustic linear antennas.

TECHNOLOGICAL BACKGROUND

It is sought more particularly here below in this document to describe problems existing in the field of seismic data acquisition for oil prospecting industry. The invention of course is not limited to this particular field of application but is of interest for any technique that has to cope with closely related or similar issues and problems.

The operations of acquiring seismic data in the field conventionally use networks of seismic sensors, like accelerometers, geophones or hydrophones. In a context of seismic data acquisition in a marine environment, these sensors are distributed along cables in order to form linear acoustic antennas normally referred to as "streamers" or "seismic streamers". The network of seismic streamers is towed by a seismic vessel.

The seismic method is based on analysis of reflected seismic waves. Thus, to collect geophysical data in a marine environment, one or more submerged seismic sources are activated in order to propagate seismic wave trains. The pressure wave generated by the seismic sources passes through the column of water and insonifies the different layers of the sea bed. Part of the seismic waves (i.e. acoustic signals) reflected are then detected by the sensors (e.g. hydrophones) distributed over the length of the seismic streamers. These acoustic signals are processed and retransmitted by telemetry from the seismic streamers to the operator station situated on the seismic vessel, where they are stored.

A well-known problem in this context is the positioning of the seismic streamers. Indeed, it is important to precisely locate the streamers in particular for:

monitoring the position of the sensors (hydrophones) in order to obtain a satisfactory precision of the image of the sea bed in the exploration zone; and detecting the movements of the streamers with respect to one another (the streamers are often subjected to various external natural constrains of variable magnitude, such as the wind, waves, currents); and monitoring the navigation of streamers.

In practice, it is aimed to carry out an analysis of sea bed with a minimum number of passages of the vessel in the concerned area. For that purpose, the number of streamers implemented in the acoustic network is substantially increased. This problem of localization of streamers is thus particularly noticeably especially in view of the length of the streamers, which may vary between 6 and 15 kilometers, for example.

Control of the positions of streamers lies in the implementation of navigation control devices (commonly referred as "birds") installed at regular intervals (every 300 meters for example) along the seismic streamers.

Birds of the prior art are used to control only the depth of the streamers in immersion. Today, the birds are used to control the depth as well as the lateral position of the streamers.

The FIG. 1 shows a configuration of a part of a streamer 13 which comprises a series of sensors (hydrophones) 16, an electro-acoustic transducer 14 (described in more details thereafter) and a bird 10 distributed along its length.

A complete streamer 13 comprises (along its length) a multitude of parts described on FIG. 1, and thus comprises a huge number of sensors (hydrophones) 16 and a series of electro-acoustic transducers 14.

Each bird 10 may be associated with an electro-acoustic transducer 14 and comprises a body 11 equipped with at least one motorized pivoting wings 12 making it possible to steer laterally the streamer 13 and control the immersion depth of the streamer 13.

The control of the birds is made locally or by a master controller situated onboard the vessel.

An acoustic node is commonly known as being a transducer 14 and it's associated electronic. A bird 10 may be associated with an acoustic node 17 to allow this acoustic node to ensure a local control function of the associated streamer 13.

For the horizontal driving, the electro-acoustic transducers 14 allow to estimate the distances between acoustic nodes (named here below "inter-node distances") placed along two different streamers 13, adjacent or not. More precisely, an electro-acoustic transducer 14 of a first streamer sends several first acoustic sequences and also receives several second acoustic sequences coming from a second electro-acoustic transducer 14 of a second streamer, adjacent or not relative to said first streamer. To estimate an inter-node distance, the data received by a transducer 14 of an acoustic node are then processed locally by an electronic module (not shown on FIG. 1) associated with the transducer 14 or processed by a master controller onboard the vessel.

Transducers 14 are transmitters and receivers of acoustic sequences (i.e. acoustic signals in the form of modulated bits) used to determine distances between adjacent nodes situated on the various streamers, thereby forming a mesh of inter-node distances, in order to know precise lateral positioning of all the streamers.

Transducer here is understood to mean either a single electroacoustic device consisting of a transceiver (emitter/receiver) of acoustic signals, or a combination of a sender device (e.g. a pinger) and a receiver device (e.g. a pression particle sensor (hydrophone) or a motion particle sensor (accelerometer, geophone . . . )).

Usually, each node comprises an electro-acoustic transducer enabling it to behave alternately as a sender node and as a receiver node (for the transmission and the reception, respectively, of acoustic signals). In an alternative embodiment, a first set of nodes act only as sender nodes and a second set of nodes act only as receiver nodes. A third set of nodes can also be used in combination with the first and second sets of nodes. The inter-node distance between two synchronized nodes A and B can be typically estimated on the basis of the following formula:

$$d_{AB} = k \times t_{AB}$$

with:
$d_{AB}$, the inter-node distance separating a sender node (A) from a receiver node (B) of the acoustic signal;
$t_{AB}$, the propagation duration elapsed between the emission instant and reception instant of the acoustic signal transmitted from the sender node (A) to the receiver node (B);
k, a "measured" or "estimated" value of sound velocity.

As already said, the control of the birds is made locally or by a master controller situated onboard the vessel.

Nowadays, a method widely known for obtaining underwater acoustic sound velocity (or sound velocity for simplification) of acoustic signals transmitted in an acoustic network is the use of sound velocimeters. Indeed, the measurements of sound velocity used by the navigation system are, in general, carried out by means of two sound velocimeters each arranged to two distinct extremities of the network of streamers, thereby providing "measured values" (also called "true values"). By way of example, FIG. 2 shown a network of ten streamers, referred from 20a to 20j, towed by a vessel 21 on which is located a centralized system (not shown) comprising a navigation system and a node manager system. Two velocimeters 22, 23 are positioned on the two outmost streamers 20a and 20j of the set of streamers towed by the vessel, the first one 22 being positioned near the vessel, the second one 23 being positioned at the opposite of the vessel. An estimation of the sound velocity is then carried out by the navigation system at each point corresponding to a position of an acoustic node by observation of the history of real measurements of sound velocity provided by the velocimeters, while taking into account the speed of the vessel.

A drawback of this known method is that, if one of the two velocimeters breaks down, it is necessary to raise the streamer (in which this velocimeter is comprised) out of water, in order to be able to change or repair the defective velocimeter.

Another drawback of this known method is that, to estimate sound velocity of acoustic signals, the navigation system has to suppose that the measured value of sound velocity in a given fixed point is constant over time (in the axis of the streamers). However, in view of the considerable length of the streamers and the low speed of the vessel, there can be several hours elapse between the sound velocity measurement carried out in that given point and the passage of an acoustic node at that same given point. The sound velocity of an acoustic wave in water being, in general, a parameter that rapidly changes particularly with temperature, pressure and salinity of water. Thus, this estimation method provides sound velocity values that are not always reliable. Based on the principle that the average sound velocity of the seawater is equal to 1500 m·s$^{-1}$, the inventors found that the error in the value of celerity estimated for each acoustic node may frequently reach a few percents, thereby causing an error in propagation duration measurement, and hence in inter-node distance measurement, that may reach the same percentage. It follows that the localization of sensors (hydrophones) distributed along the seismic streamers lacks therefore of precision.

Another drawback of this known method is that the sound velocity measured by a velocimeter to a given point is considered as being constant in the transverse plan to the axis of the streamers (cross-line measurements). For instance, for a network of ten streamers separated each other from 100 meters, the sound velocity is supposed to be constant over the width of network, i.e. 1000 meters. Thereby an approximation, for example by linear or polynomial interpolation, of the sound velocity measured by each velocimeter is carried out in the transverse plan to the axis of the streamers, also making the estimated values of sound velocity unreliable.

In addition, independently of the navigation system, the birds placed along the streamers comprise embedded electronics used for implementing locally a feedback loop (in order to control inter-node distances of the acoustic network). As said before, these inter-node distances are determined as function of the propagation duration of transmitted acoustic signals measured by nodes of the network and an estimated value of sound velocity which is provided, either by the navigation system, or by an operator via the node manager system. The error in this estimated value of sound velocity may therefore cause an error in the feedback of the nodes between themselves.

Another well-known method of estimation of acoustic signal sound velocity consists in measuring in-line propagation duration between two nodes placed on a same streamer and, from knowledge of the in-line distance separating the two nodes, deducing a estimated value of sound velocity. However, in-line propagation duration measurement requires a node structure with an electro-acoustic transducer deported from the streamer (i.e. placed outside the node). Such a known method can not therefore be implemented in the context of network of streamers with transducers integrated into the streamers. Indeed, because of the presence of metallic bodies on some of the streamers, the omnidirectional radiation configuration (or pattern) of transducers is made quasi-omnidirectional or directive, perpendicularly to the axis of the streamers, rendering implementation of the in-line propagation duration measurements impossible.

It should be reminded that the aforesaid problem is described in the particular field of seismic prospecting in a marine environment, but it can be applied in other fields of application.

SUMMARY

A particular embodiment of the invention proposes a method for estimating an underwater acoustic sound velocity in a network of acoustic nodes arranged along towed acoustic linear antennas and in which a plurality of acoustic signals are transmitted between the nodes, the method being characterized in that it comprises steps of:
obtaining two predetermined distances each separating a couple of nodes placed along a same first acoustic linear antenna;
for each couple of first and second nodes, obtaining:
a first propagation duration of an acoustic signal transmitted between said first node and a third node placed along a second acoustic linear antenna;
a second propagation duration of an acoustic signal transmitted between said second node and said third node;

estimating said underwater acoustic sound velocity, as a function of said two predetermined distances and said first and second propagation durations obtained for each couple of nodes.

Thus, this particular embodiment relies on a wholly novel and inventive which either avoids the use of velocimeters in the acoustic network or allows to refine the values of sound velocity measured by velocimeters used in the acoustic network.

This particular embodiment is also more robust than the known solution based on velocimeters. Indeed, in the known solution, if one of the two velocimeters breaks down, it is necessary to raise the streamer (in which this velocimeter is comprised) out of water. With the proposed solution, if a node can not carry out the method, the other nodes are able to do it, without the need to raise the streamer.

According to a particular feature, the method comprises steps of:

a) obtaining a first couple of first node groups, each first node group comprising one of said couples of first and second nodes and the corresponding third node, and each first node group being associated to a triangle having as vertexes said first, second and third nodes, a same third node being common to said first node groups;

b) for each first node group, obtaining:
   said first propagation duration of an acoustic signal transmitted between said third and first nodes;
   said second propagation duration of an acoustic signal transmitted between said third and second nodes;
   the predetermined distance separating said first and second nodes;

c) estimating said underwater acoustic sound velocity, as a function of the first and second propagation durations and the predetermined distance obtained for each first node group, and assuming that the heights, passing through said third node, of the two triangles associated with the first couple of first node groups are equal.

The general principle of this particular embodiment is therefore that of forming a couple of groups of nodes constituting two triangles, and searching for the acoustic sound velocity at a common node level based on the principle that the heights, passing through the common third node, of the two triangles are equal.

According to an advantageous feature, the first node groups comprise a common node arranged along said first acoustic linear antenna.

Thus, the two triangles obtained, ABD and BCD, comprise, besides the common node D (which is arranged along the first acoustic linear antenna), a common node B (which is arranged along the second acoustic linear antenna), thus easing the calculations required for sound velocity estimation.

Advantageously, said step of estimating said underwater acoustic sound velocity is based on the following formula:

$$k = \sqrt{\left| \frac{AB \cdot BC(AB+BC)}{t_{AD}^2 BC - t_{BD}^2(AB+BC) + t_{CD}^2 AB} \right|}$$

with:

k, the estimated underwater acoustic sound velocity;

AB, the first predetermined distance separating the first node A and the second node B of the first node group ABD;

BC, the first predetermined distance separating the first node B and the second node C of the first node group BCD;

$t_{AD}$, the first propagation duration of an acoustic signal transmitted between the third node D and the first node A for the first node group ABD;

$t_{CD}$, the second propagation duration of an acoustic signal transmitted between the third node D and the second node C for the first node group BCD;

$t_{BD}$, the second propagation duration of an acoustic signal transmitted between the third node D and the second node B for the first node group ABD or the first propagation duration of an acoustic signal transmitted between the third node D and the first node B for the first node group BCD.

Advantageously, said second acoustic linear antenna is adjacent to said first acoustic linear antenna.

This contributes to the improvement of accuracy in propagation duration measurements, thereby ensuring the provision of a reliable sound velocity estimation. Indeed, the inter-node distances (between nodes placed along different acoustic linear antennas) are lower, and the corresponding propagation durations (between these nodes) are also lower.

Advantageously, said steps a), b) and c) are carried out for at least two first couples of first node groups, enabling to obtain a first estimation of said acoustic sound velocity for each of said first couples. Said method comprises a step of determining a final estimation of said underwater acoustic sound velocity, as a function of said first estimations.

By obtaining further first estimations of sound velocity with several couples of node groups, it is thus possible to carry out a processing (statistic analysis) of these estimations to refine the final estimation. In case of average of the set of obtained estimations for example, the greater the number of estimations, the less the standard deviation is.

According to an advantageous feature, the method comprises steps of:

a') obtaining a second couple of second node groups, each second node groups comprising said third node and a fourth node and a fifth node arranged along a third acoustic linear antenna, each second node group being associated to a triangle having as vertexes said third, fourth and fifth nodes;

b') for each second node group, obtaining:
   a third propagation duration of an acoustic signal transmitted between said third node and said fourth node;
   a fourth propagation duration of an acoustic signal transmitted between said third node and said fifth node;
   a predetermined distance separating said fourth and fifth nodes;

c') estimating an underwater acoustic sound velocity, as a function of the third and fourth propagation durations and said second predetermined distance obtained for each second node group, and assuming that the heights, passing through said third node, of the two triangles associated with the second couple of second node groups are equal;

said steps a), b) and c) enable to obtain a first estimation of said underwater acoustic sound velocity and said steps a'), b') and c') enable to obtain a second estimation of said underwater acoustic sound velocity, and that said method comprises a step of determining a final estimation of said underwater acoustic sound velocity, as a function of said first and second estimations.

Another couple of node groups can be formed from the second and third acoustic linear antennas, enabling to obtain a second estimation other than the first estimation of the acoustic sound velocity obtained by means of node groups arranged along the first and second acoustic linear antennas. This ensures the provision of a reliable sound velocity value.

Advantageously, said steps a'), b') and c') are carried out for at least two second couples of second node groups, enabling to obtain a second estimation of said underwater acoustic sound velocity for each of said second couples. Moreover, said method comprises a step of determining a final estimation of said acoustic sound velocity, as a function of said first estimation or estimations and said second estimations.

By obtaining further second estimations of sound velocity with several couples of node groups, accuracy of the final estimation of sound velocity is improved even more.

According to an advantageous feature, said first and third acoustic linear antennas are not placed on a same side of said second acoustic linear antenna.

In case of non-null radius of curvature of the acoustic linear antennas, the possible error occurred on sound velocity estimation obtained with the first node groups arranged along the first and second antennas is compensated by the possible error occurred on sound velocity estimation obtained with the second node groups arranged along the second and third antennas.

Advantageously, the method is implemented by a device belonging to the group comprising: said third node and a centralized system.

In another embodiment of the invention, there is proposed a computer program product comprising program code instructions for implementing the above-mentioned method (in any one of its different embodiments) when said program is executed on a computer.

In another embodiment of the invention, there is proposed a computer-readable storage means storing a computer program comprising a set of instructions executable by a computer to implement the above-mentioned method (in any one of its different embodiments).

In another embodiment of the invention, there is proposed a device for estimating an underwater acoustic sound velocity in a network of acoustic nodes arranged along towed acoustic linear antennas and in which a plurality of acoustic signals are transmitted between the nodes. The device comprises:
- means for obtaining two predetermined distances each separating a couple of nodes placed along a same first acoustic linear antenna;
- means for obtaining, for each couple of first and second nodes:
  - a first propagation duration of an acoustic signal transmitted between said first node and a third node placed along a second acoustic linear antenna;
  - a second propagation duration of an acoustic signal transmitted between said second node and said third node;
- means for estimating said underwater acoustic sound velocity, as a function of said two predetermined distances and said first and second propagation durations obtained for each couple of nodes.

LIST OF FIGURES

Other features and advantages of embodiments shall appear from the following description, given by way of an indicative and non-exhaustive example, and from the appended drawings, of which:

FIG. 1 already described with reference to the prior art, presents an example of the structure of an acoustic node arranged along a streamer;

FIG. 2 already described with reference to the prior art, shows an example of network of acoustic streamers towed by a vessel in the context of seismic prospecting in a marine environment;

DETAILED DESCRIPTION

In all the figures of the present document, the identical elements and steps are designated by a same numerical reference.

Figure 1:
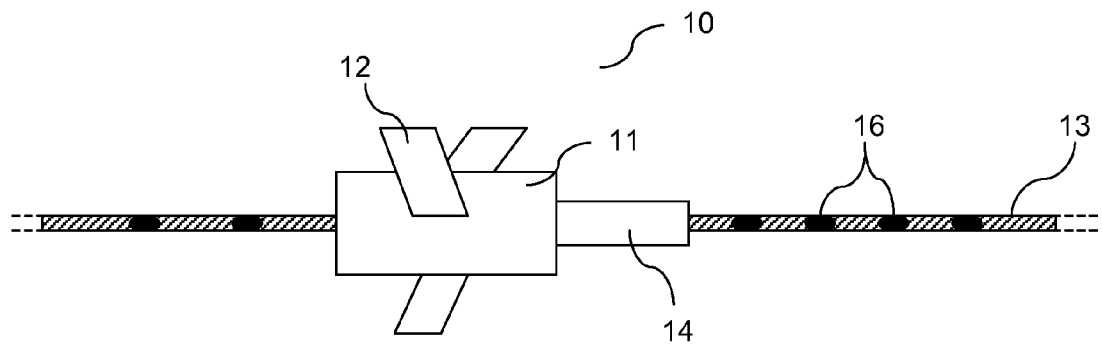
Figure 2:
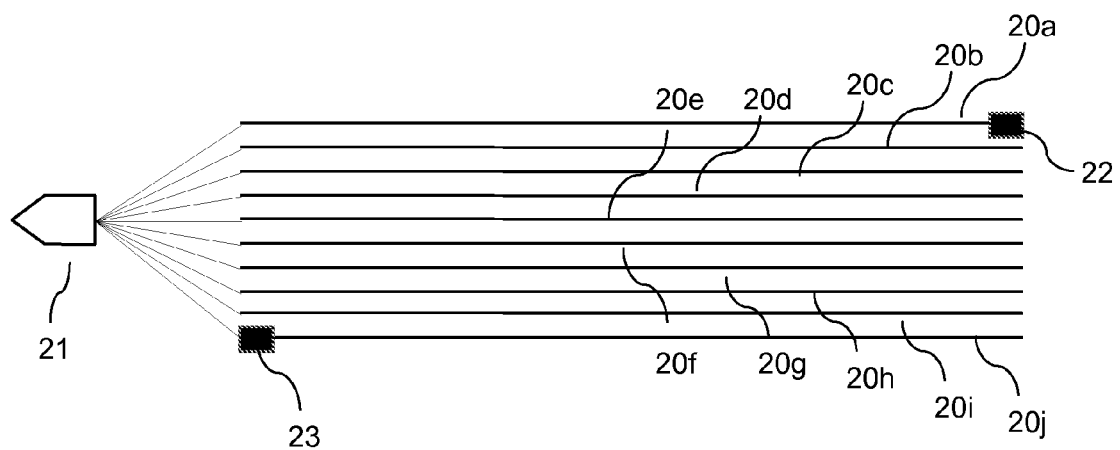

FIGS. 1 and 2 have been already described above in relation with the prior art.

Figure 3:
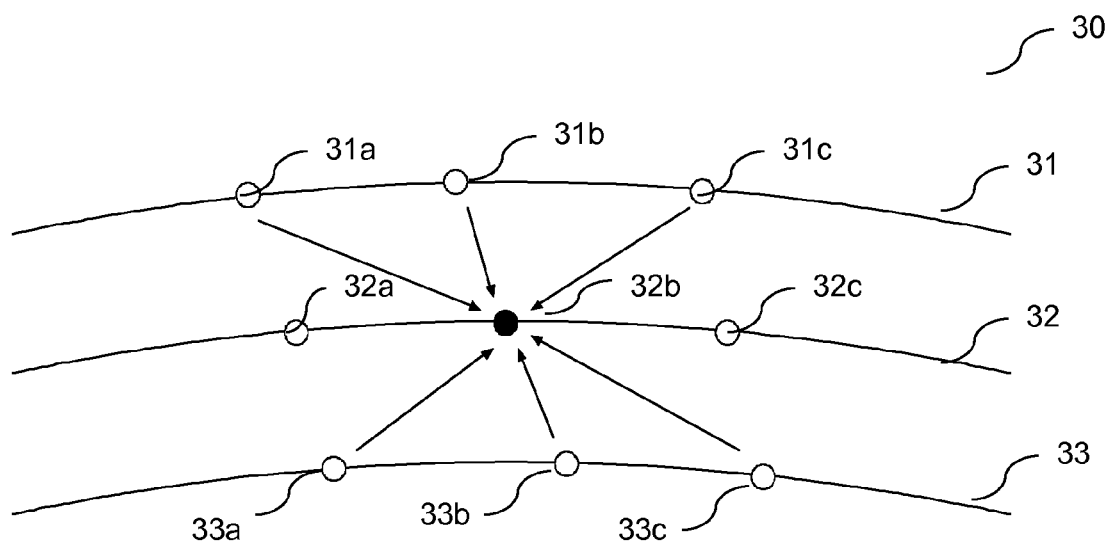
FIG. 3 illustrates an example of a network of acoustic nodes in which the method of estimation is implemented, according to a particular embodiment of the invention.

FIG. 3 illustrates an example of a network 30 of acoustic nodes in which the method of estimation is implemented, according to a particular embodiment of the invention.

More particularly, this network here illustrates an acoustic communications system comprising a set of three streamers 31, 32, 33, in a curve or in presence of lateral currents, on each of which are arranged three acoustic nodes: the nodes, referenced as 31a, 31b, 31c for the streamer 31, the nodes 32a, 32b, 32c for the streamer 32 and the nodes 33a, 33b, 33c for the streamer 33. Each node is capable of behaving alternately as a sender node and as a receiver node and having an electro-acoustic transducer for the transmission and reception of acoustic signals. It is here considered that each sender node sends an acoustic signal (represented by an arrow in the figure) according to a quasi-omnidirectional radiation pattern that enables to reach a maximum number of acoustic nodes within the network. The node 32b here behaves as a receiver node and the nodes 31a, 31b, 31c, 33a, 33b, 33c arranged along the two streamers 31 and 33 placed on both sides of the streamer 32 behave as sender nodes.

It should be noted that the number of acoustic nodes shown in FIG. 3, as well as the number of streamers, is deliberately limited by way of a purely pedagogical description, so as not to burden the figure and the associated description. It is clear however that the invention can be implemented in the context of an application with an acoustic network comprising a greater number of nodes and streamers. Also, some acoustic nodes of the network may not be necessarily equipped with a bird 10 for steering the streamers (as illustrated on FIG. 1), but only with an electro-acoustic transducer 14 and an associated electronic module (not shown) which allows to transmit and receive acoustic sequences.

The acoustic network relies on time, frequency and space access mode (i.e. time, frequency and spatial discrimination).

The principle of time discrimination is that of sub-dividing the available time into several time slots or speech times which are allocated to the different nodes of the network: each node of the network has cyclically a speech time during which it transmits its acoustic signal. When a node transmits an acoustic signal, all the other nodes can listen to it.

The principle of frequency discrimination is that of using multiple frequency bands for the emission of acoustic signals, each frequency band being allocated to determined nodes of the network.

We call spatial discrimination the fact that two distant nodes can emit in the same time slot and in the same frequency bandwidth if the two acoustic sequences arrive at different instants on the receivers. Therefore there isn't any interference between the acoustic sequences and the receiver is able to process each independently.

Some birds 10 may comprise embedded electronics used for implementing a feedback loop in order to control inter-node distances of the acoustic network. Inter-node distances are determined as function of the propagation durations of acoustic signals transmitted from each node 31a, 31b, 31c, 33a, 33b, 33c to the node 32 placed on the streamer 32, and a value of sound velocity obtained by the implementation of the method of estimation according to an embodiment of the invention (the principle of which is explained below).

Figure 4:
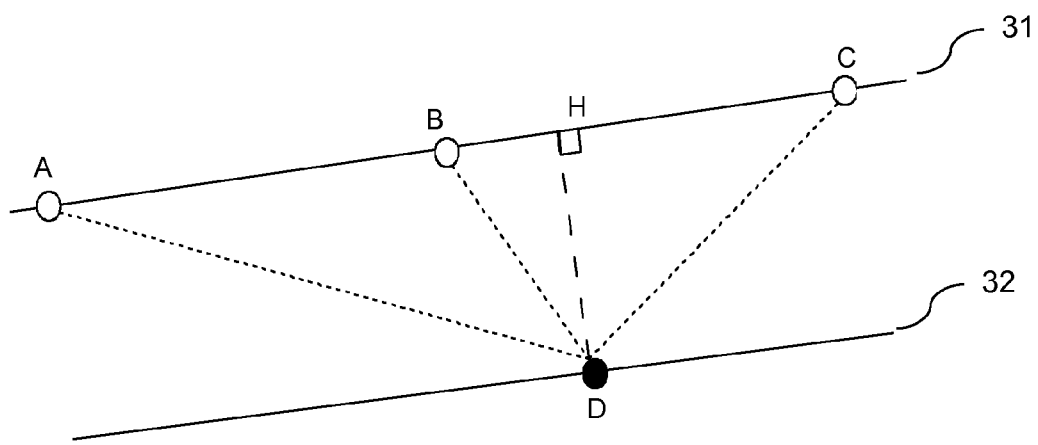
FIG. 4 is a simplified schematic representation illustrating a method of calculation of acoustic sound velocity, according to a first embodiment of the invention.

FIG. 4 is a simplified schematic representation illustrating a method of calculation of acoustic sound velocity, according to a first embodiment of the invention.

Here below, it is considered that the points A, B, C and D correspond respectively to the acoustic nodes 31a, 31b, 31c and 32b of the network illustrated in FIG. 3, arranged along the streamers 31 and 32. But, for reasons of simplification of description and calculation of sound velocity, the radius of curvature of each of the streamers 31 and 32 is here considered as being null.

Only two streamers are thereby involved in this particular embodiment. In particular, the aim is to estimate a sound velocity value at point D in cooperation with the three nodes A, B, C. The node D is also named as common node, this latter being common to both triangles ABD and BCD.

Let UVW be an arbitrary triangle, with sides UV=c, VW=a, UW=b and height WH=h. By Heron's formula, the area of this triangle is:

$$\text{Aera}_{UVW} = \sqrt{s(s-a)(s-b)(s-c)}$$

where $$s = \frac{1}{2}(a+b+c)$$

is half of the triangle's perimeter.
But the area of a triangle can also be written with the well-known formula:

$$\text{Aera}_{UVW} = \frac{c \cdot h}{2}$$

where c is the length of the base of the triangle UVW.
From these two above formulas for calculating area of the triangle UVW, we obtain the following:

$$s(s-a)(s-b)(s-c) = \frac{c^2 h^2}{4}$$

which, after simplifying, leads to the following formula (I):

$$h^2 = -\frac{(a+b+c)(a+b-c)(a-b-c)(a-b+c)}{4c^2} \quad \text{(I)}$$

For the triangle ABD (first group of nodes), the aforesaid formula (I) leads to the following:

$$HD^2 = -\frac{(BD+AD+AB)(BD+AD-AB)(BD-AD-AB)(BD-AD+AB)}{4 \cdot AB^2}$$

For the triangle BCD (second group of nodes), the aforesaid formula (I) leads to the following:

$$HD^2 = -\frac{(CD+BD+BC)(CD+BD-BC)(CD-BD-BC)(CD-BD+BC)}{4 \cdot BC^2}$$

According to an embodiment of the present invention, the method of estimation consists in searching for the sound velocity for the node D such that heights of the triangles ABD and BCD are identical. In that simplified schematic representation of FIG. 4, it should be noted that HD represents the common height of the two triangles ABD and BCD passing through the node D, since the radius of curvature of the two streamers 31 and 32 is null. Thus, after equalizing the two above formulas, we obtain in our case:

$$\frac{(BD+AD+AB)(BD+AD-AB)(BD-AD-AB)(BD-AD+AB)}{AB^2} = \frac{(CD+BD+BC)(CD+BD-BC)(CD-BD-BC)(CD-BD+BC)}{BC^2}$$

Next, expressing the inter-node distances AD, BD and CD respectively as:

$$AD = k \cdot t_{AD}, \text{ with:}$$

k, the acoustic signal sound velocity at point D [in m/s];
$t_{AD}$, the propagation duration of acoustic signal elapsed between nodes A and D [in s];

$$BD = k \cdot t_{BD}, \text{ with:}$$

k, the acoustic signal sound velocity at point D [in m/s];
$t_{BD}$, the propagation duration of acoustic signal elapsed between nodes B and D [in s];

$$CD = k \cdot t_{CD}, \text{ with:}$$

k, the acoustic signal sound velocity at point D [in m/s];
$t_{CD}$, the propagation duration of acoustic signal elapsed between nodes C and D [in s].

Next, we have:

$$\frac{(k \cdot t_{BD} + k \cdot t_{AD} + AB)(k \cdot t_{BD} + k \cdot t_{AD} - AB)(k \cdot t_{BD} - k \cdot t_{AD} - AB)(k \cdot t_{BD} - k \cdot t_{AD} + AB)}{AB^2} = \frac{(k \cdot t_{CD} + k \cdot t_{BD} + BC)(k \cdot t_{CD} + k \cdot t_{BD} - BC)(k \cdot t_{CD} - k \cdot t_{BD} - BC)(k \cdot t_{CD} - k \cdot t_{BD} + BC)}{BC^2}$$

Then:

$$k^4 \cdot \frac{t_{AD}^4 - 2 \cdot t_{AD}^2 \cdot t_{BD}^2 + t_{BD}^4}{AB^2} - 2 \cdot k^2 \cdot (t_{AD}^2 + t_{BD}^2) + AB^2 =$$

$$k^4 \cdot \frac{t_{BD}^4 - 2 \cdot t_{BD}^2 \cdot t_{CD}^2 + t_{CD}^4}{BC^2} - 2 \cdot k^2 \cdot (t_{CD}^2 + t_{BD}^2) + BC^2$$

Then denoting $Z=k^2$, we obtain the following polynomial equation:

$$Z^2 \cdot \left(\left(\frac{t_{AD}^2 - t_{BD}^2}{AB}\right)^2 - \left(\frac{t_{BD}^2 - t_{CD}^2}{BC}\right)^2\right) - 2 \cdot Z(t_{AD}^2 - t_{CD}^2) + AB^2 - BC^2 = 0$$

This polynomial equation of a degree 2 presents two solutions:

$$Z = \frac{AB \cdot BC(AB + BC)}{BC(t_{AD}^2 - t_{BD}^2) - AB(t_{BD}^2 - t_{CD}^2)} \quad (1)$$

$$Z = \frac{AB \cdot BC(AB - BC)}{BC(t_{AD}^2 - t_{BD}^2) + AB(t_{BD}^2 - t_{CD}^2)} \quad (2)$$

According to equations (1) and (2), we obtain the following mathematical formula (II):

$$k = \sqrt{\left|\frac{AB \cdot BC(AB + BC)}{t_{AD}^2 BC - t_{BD}^2 (AB + BC) + t_{CD}^2 AB}\right|} \quad (II)$$

Such a formula expresses the relationship between the acoustic sound velocity k estimated for the common node D, the propagation durations elapsed for acoustic signals transmitted between nodes A and D ($t_{AD}$), between nodes B and D ($t_{BD}$), between nodes C and D ($t_{CD}$), and the distances AB and BC respectively separating node A from node B and node B from node C.

The common node D, acting here as a receiver node (as illustrated on FIG. 3), knows the propagation durations $t_{AD}$, $t_{BD}$ and $t_{CD}$. Indeed, the node D is equipped with a transducer (like transducer 14 of FIG. 1) and associated electronic module (not shown) which enable it to measure the propagation durations $t_{AD}$, $t_{BD}$ and $t_{CD}$ of the acoustic signals received from the nodes A, B and C. Furthermore, the common node D previously knows the distances AB and BC since they were initially defined when designing the streamer 31. Therefore, from knowledge of the distances AB and BC, and propagation durations $t_{AD}$, $t_{BD}$, $t_{CD}$, the node D is capable to carry out an estimation of the sound velocity k in the neighborhood of point D. In other words, this sound velocity estimation is considered as being the same in the area of the couple of the node groups ABD and BCD.

In that particular embodiment of the invention described above, the process of calculation of the sound velocity k is therefore implemented by the node D, which cooperates with three other nodes (A, B, C) placed on another single streamer. Two node groups of three nodes (A,B,D and B,C,D) are then obtained to form two triangles (ABD and BCD). The two node groups having a common node B arranged along the streamer 31, calculations for estimating the acoustic sound velocity is therefore simplified. Indeed, one may envisage in variant that the node D cooperates with an additional node placed on this streamer 31, such as a node B'. The two groups of three nodes obtained could be A,B,D and B',C,D to form two triangles ABD and B'CD, which means that more propagation duration measurements are needed, namely $t_{AD}$, $t_{BD}$, $t_{CD}$, $t_{B'D}$.

For the calculation of the sound velocity k at the node D, one may envisage in variant that the node D cooperates with more than three nodes placed on the same streamer 31. Other couples of groups of three nodes can thus be formed which allow to obtain several estimations of sound velocity. Each couple of node groups formed enables to obtain an estimation of sound velocity based on the principle of calculation described above. The sound velocity estimated for the node D is the average of the set of estimations of sound velocity, thus reducing the sound velocity standard deviation and improving the accuracy of the final estimation of sound velocity.

In a variant of the embodiment, the measurements of propagation durations are first transmitted, via the communication bus integrated directly into the streamer, from the node D to the centralized system placed on the vessel, so that the centralized system takes in charge of carrying out the estimation of sound velocity k at point D. The estimation of sound velocity is not local (i.e. at the node D level) but is deported and implemented at the centralized system level, it being understood that the inline inter-node distances are previously known. In that way, the centralized system can decide to refine or replace the sound velocity values measured and provided by the velocimeters arranged on the streamers, by exploiting the propagation duration measurements provided by the nodes of the network.

We may note that the propagation times used for the sound velocity computation can be 1-way or 2-way. We call "1-way" a propagation time in one direction between two acoustic nodes (per example from A to D or D to A) and "2-way" the mean of two propagation times in both directions. Therefore it may be envisaged that the propagation times are performed by the node A, B and C in place of D. In that case, the sound velocity estimation at the acoustic node D location can be carried out by the centralized system.

Figure 5:
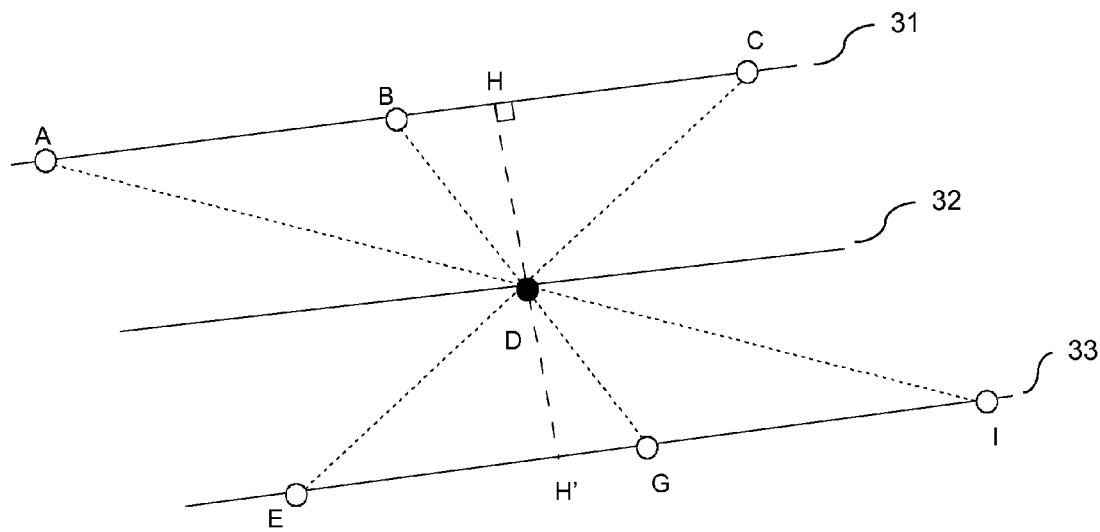
FIG. 5 is a simplified schematic representation illustrating a method of calculation of acoustic sound velocity, according to a second embodiment of the invention.

FIG. 5 is a simplified schematic representation illustrating a calculation method of acoustic sound velocity, according to a second embodiment of the invention.

In that particular embodiment, the calculation of sound velocity k is implemented by the node D, which cooperates with six nodes arranged along two streamers 31, 33: three nodes A, B, C are arranged along a streamer 31 and three nodes E, G, I are arranged along a streamer 33. These two streamers 31 and 33 are placed on both sides of the streamer 32 where the common node D is. Thus, contrary to the particular embodiment of FIG. 4, an additional streamer comprising a set of three nodes is involved in the process of calculation of sound velocity for the node D.

For reasons of simplification of description and calculation of sound velocity, the radius of curvature of each of the streamers 31, 32, 33 is here considered as being null.

HD represents the heights of the triangles ABD and BCD passing through node D and H'D represents the heights of the triangles EGD and GID passing through node D.

The triangles ABD and BCD corresponds to a first couple of node groups A,B,D and B,C,D. By application of the formula (II) used in this embodiment as in FIG. 4 for the triangles ABD and BCD, we obtain the following:

$$k_1 = \sqrt{\left|\frac{AB \cdot BC(AB + BC)}{t_{AD}^2 BC - t_{BD}^2 (AB + BC) + t_{CD}^2 AB}\right|}$$

The triangles EGD and GID corresponds to a second couple of node groups E,G,D and G,I,D. Based on the same reasoning as in FIG. 4 with the height H'D, the aforesaid formula (II) becomes for the triangles EGD and GID:

$$k_2 = \sqrt{\left|\frac{EG \cdot GI(EG+GI)}{t_{ID}^2 EG - t_{GD}^2(EG+GI) + t_{ED}^2 GI}\right|}$$

The final estimation of sound velocity calculated at point D is the average of the sound velocity estimations obtained for the first and second couples of node groups, $$k = \frac{k_1 + k_2}{2}$$

By reducing the sound velocity standard deviation, this improves the accuracy of sound velocity estimated by the node D.

This particular embodiment is particularly robust to deal with eventual situations in which streamers present a non-zero radius of curvature. As a matter of fact, in practice, streamers may band confronted with a lateral current or a change of direction (a curve) of the vessel for example, and an error in the estimated value of sound velocity may be induced. It is based on the assumption that the radiuses of curvature of the streamers are substantially identical: thereby, the increased error obtained on first sound velocity calculation based on streamer 31 ($k_1$) is compensated by the decreased error obtained on sound velocity calculation based on streamer 33 ($k_2$) and vice versa. Therefore, even in case of non-zero radius of curvature of streamers, the sound velocity estimation remains accurate.

It should be noted that streamers 31, 33 involved in sound velocity calculation method illustrated in FIGS. 4 and 5 are adjacent to the streamer 32 where the sound velocity calculation is carried out. It should be noted that the invention is not limited to such an implementation, but that it can also be implemented in an acoustic network involving nonadjacent streamers or combination of adjacent and nonadjacent streamers to the streamer where the sound velocity calculation is carried out. In case of estimation carried out for couple(s) of node groups placed on adjacent streamers, this however contributes to the improvement of accuracy in propagation duration measurements (streamers being separated from each other by a relatively short distance), thereby ensuring the provision of more accurate sound velocity values.

Figure 6:
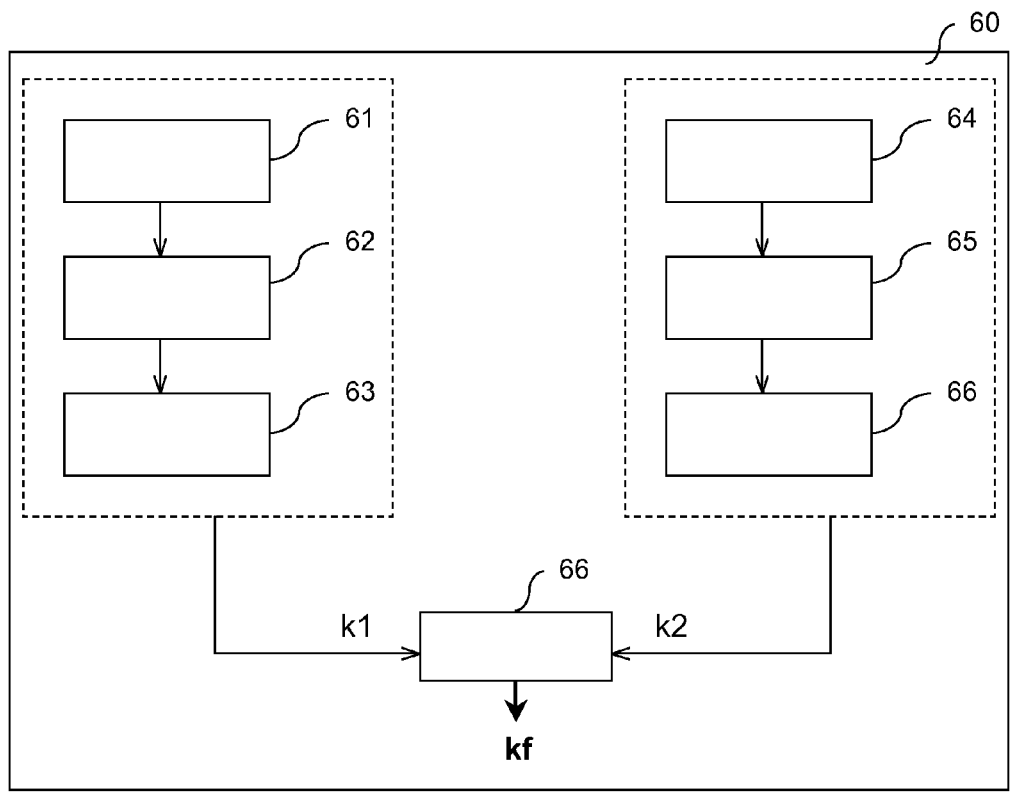
FIG. 6 is a generic view of a flowchart of an algorithm for implementing the method of estimation according to a particular embodiment of the invention.

FIG. 6 is a generic view of a flowchart of an algorithm 60 for implementing the method of estimation according to a particular embodiment of the invention.

In a step 61, a first couple of groups of three nodes is obtained. Every node groups comprises a first common node (e.g. node D) arranged along a first streamer. Each node group of the first couple comprises a second node (A or B) and a third node (B or C) arranged along a second streamer and is associated to a triangle (ABD or BCD) having as vertexes the first, second and third nodes.

In a step 62, a first propagation duration of an acoustic signal transmitted between the first and second nodes, a second propagation duration of an acoustic signal transmitted between the first and third nodes, as well as a predetermined distance separating the second and third nodes are obtained for each node group formed in the previous step.

In step 63, a first acoustic signal sound velocity estimation, referred as k1, is carried out for the first node (D) as a function of the first and second propagation durations and the predetermined distance separating the second and third nodes, based on the principle described in FIG. 4. This principle consisting in assuming that the heights, passing through the first node D, of the two triangles (ABD and BCD) associated with the two node groups are equal.

The steps 61 to 63 therefore concerns a first couple of node groups for which a first estimation (k1) of sound velocity is obtained.

The steps 64 to 66 concerns a second couple of groups of three for which a second estimation (k2) of sound velocity is obtained. The steps 64 to 66 can be carried out in parallel with the steps 61 to 63.

In a step 64, a second couple of groups of three nodes is obtained. Every node groups also comprises the first common node (D) arranged along a first streamer. Each node group of that second couple comprises a fourth node (E or G) and a fifth node (G or I) arranged along a third streamer and is associated to a triangle (EGD or GID) having as vertexes the first, second and third nodes.

In a step 65, a third propagation duration of an acoustic signal transmitted between the first and fourth nodes, a second propagation duration of an acoustic signal transmitted between the first and fourth nodes, as well as a predetermined distance separating the fourth and fifth nodes are obtained for each node group formed in the previous step 64.

In step 66, a second estimation (k2) of acoustic sound velocity is carried out for the first node (D) as a function of the first and second propagation durations and the predetermined distance separating the fourth and fifth nodes, based on the principle described in FIG. 4. This principle consisting in assuming that the heights, passing through the first node D, of the two triangles (EGD or GID) associated with the two node groups are equal.

Then, in step 67, from the first estimation (k1) obtained by implementation of the steps 61, 62, 63 and the second estimation (k2) obtained by implementation of the steps 64, 65, 66, a final estimation (kf) of sound velocity is determined by means of a given statistic processing. By way of examples, the final estimation is the average of the first and second estimations.

Figure 7:
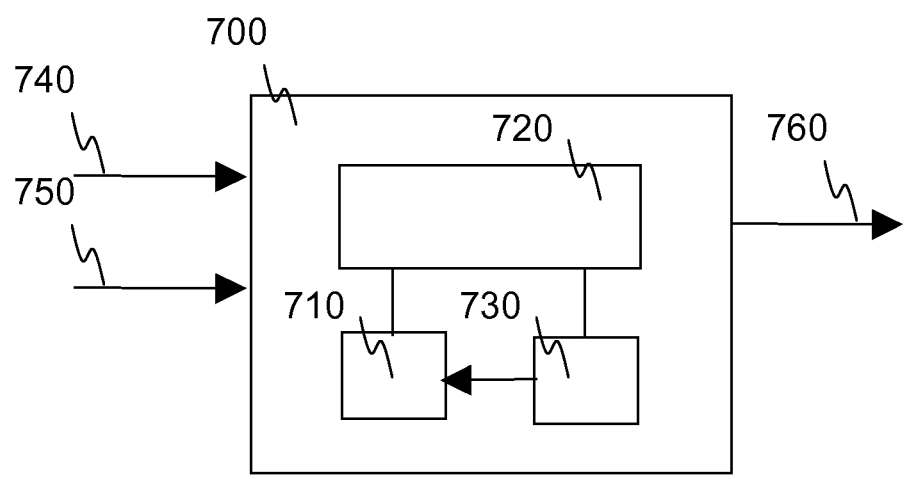
FIG. 7 shows the schematic structure of a sound velocity estimation device according to a particular embodiment of the invention.

Now referring to FIG. 7, we present the simplified structure of a sound velocity estimation device 700 according to a particular embodiment of the invention.

The sound velocity estimation device 700 can be an acoustic node (such as the node D of FIGS. 4 and 5), the node manager system or the navigation system.

The sound velocity estimation device 700 comprises:
a read-only memory (ROM) 730;
a random access memory (RAM) 710; and
a processor 720.

The read-only memory 730 stores an executable code of the programs, which, when are executed by the processor 720, enable implementation of the technique of an embodiment of the invention, e.g., the rules and operations of which are described above in connection with FIG. 6.

Upon initialization, the aforementioned program code instructions are transferred from the read-only memory 730 to the random access memory 710 so as to be executed by the processor 720. The random access memory 710 likewise includes registers for storing the variables and parameters required for this execution. The processor 720 receives propagation durations 740 of acoustic signals and a predetermined distance 750 and, according to the instructions of the aforementioned programs, delivers an estimation of the acoustic sound velocity 760.

All the steps of the method of estimation can be implemented equally well:
by the execution of a set of computer instructions executed by a reprogrammable computing machine such as a PC type apparatus, a DSP (a digital signal processor) or a microcontroller and can be stored in a storage medium that is detachable (for example a floppy disk, a CD-ROM or a DVD-ROM) or non-detachable; or else by a dedicated machine or component such as an FPGA (Field Programmable Gate Array), an ASIC (Application-Specific Integrated Circuit) or any dedicated hardware component.

At least one embodiment of the invention provides a technique for estimating acoustic signal sound velocities of acoustic nodes in a network of acoustic nodes that ensures the provision of reliable sound velocity values used by the navigation system, in order to accurately monitor the position of the sensors (hydrophones).

At least one embodiment of the invention provides a technique of this kind that avoids the use of velocimeters in the acoustic network.

At least one embodiment of the invention provides a technique that enables to refine the values of sound velocity measured by the velocimeters of the network.

At least one embodiment of the invention provides a technique of this kind that is simple to implement and costs little.

Although the present disclosure has been described with reference to one or more examples, workers skilled in the art will recognize that changes may be made in form and detail without departing from the scope of the disclosure and/or the appended claims.

The invention claimed is:

1. A method for estimating an underwater acoustic sound velocity in a network of acoustic nodes arranged along towed acoustic linear antennas and in which a plurality of acoustic signals are transmitted between the nodes, the method comprising:
   obtaining two predetermined distances each separating a couple of nodes ((A,B), (B,C)) placed along a same first acoustic linear antenna;
   for each couple of first and second nodes ((A,B), (B,C)), obtaining:
      a first propagation duration of an acoustic signal transmitted between said first node and a third node (D) placed along a second acoustic linear antenna; and
      a second propagation duration of an acoustic signal transmitted between said second node and said third node (D); and
   estimating said underwater acoustic sound velocity, as a function of said two predetermined distances and said first and second propagation durations obtained for each couple of nodes.

2. The method according to claim 1, comprising:
   a) obtaining a first couple of first node groups ((A,B,D), (B,C,D)), each first node group comprising one of said couples of first and second nodes ((A,B), (B,C)) and the corresponding third node (D), and each first node group being associated to a triangle having as vertexes said first, second and third nodes, a same third node (D) being common to said first node groups;
   b) for each first node group, obtaining:
      said first propagation duration of an acoustic signal transmitted between said third and first nodes;
      said second propagation duration of an acoustic signal transmitted between said third and second nodes;
      the predetermined distance separating said first and second nodes;
   c) estimating said underwater acoustic sound velocity, as a function of the first and second propagation durations and the predetermined distance obtained for each first node group, and assuming that the heights, passing through said third node, of the two triangles associated with the first couple of first node groups are equal.

3. The method according to claim 2, wherein the first node groups comprise a common node (B) arranged along said first acoustic linear antenna.

4. The method according to claim 3, wherein said step of estimating said underwater acoustic sound velocity is based on the following formula:

$$k = \sqrt{\left|\frac{AB \cdot BC(AB + BC)}{t_{AD}^2 BC - t_{BD}^2 (AB + BC) + t_{CD}^2 AB}\right|}$$

with:
k, the estimated underwater acoustic sound velocity;
AB, the first predetermined distance separating the first node A and the second node B of the first node group ABD;
BC, the first predetermined distance separating the first node B and the second node C of the first node group BCD;
$t_{AD}$, the first propagation duration of an acoustic signal transmitted between the third node D and the first node A for the first node group ABD;
$t_{CD}$, the second propagation duration of an acoustic signal transmitted between the third node D and the second node C for the first node group BCD;
$t_{BD}$, the second propagation duration of an acoustic signal transmitted between the third node D and the second node B for the first node group ABD or the first propagation duration of an acoustic signal transmitted between the third node D and the first node B for the first node group BCD.

5. The method according to claim 2, wherein said second acoustic linear antenna is adjacent to said first acoustic linear antenna.

6. The method according to claim 2, wherein said steps a), b) and c) are carried out for at least two first couples of first node groups, enabling to obtain a first estimation of said acoustic sound velocity for each of said first couples, and said method comprises a step of determining a final estimation of said underwater acoustic sound velocity, as a function of said first estimations.

7. The method according to claim 2, comprising:
   a') obtaining a second couple of second node groups ((E, G,D), (G,I,D)), each second node groups comprising said third node (D) and a fourth node and a fifth node arranged along a third acoustic linear antenna, each second node group being associated to a triangle having as vertexes said third, fourth and fifth nodes;
   b') for each second node group, obtaining:
      a third propagation duration of an acoustic signal transmitted between said third node and said fourth node;
      a fourth propagation duration of an acoustic signal transmitted between said third node and said fifth node;
      a predetermined distance separating said fourth and fifth nodes;
   c') estimating an underwater acoustic sound velocity, as a function of the third and fourth propagation durations and said second predetermined distance obtained for each second node group, and assuming that the heights, passing through said third node, of the two triangles associated with the second couple of second node groups are equal;
   wherein steps a), b) and c) enable to obtain a first estimation of said underwater acoustic sound velocity and said steps a'), b') and c') enable to obtain a second estimation of said underwater acoustic sound velocity, and said method comprises determining a final estimation of said underwater acoustic sound velocity, as a function of said first and second estimations.

8. The method according to claim 7, wherein steps a'), b') and c') are carried out for at least two second couples of second node groups, enabling to obtain a second estimation of said underwater acoustic sound velocity for each of said second couples, and said method comprises determining a final estimation of said acoustic sound velocity, as a function of said first estimation or estimations and said second estimations.

9. The method according to claim 8, wherein said first and third acoustic linear antennas are not placed on a same side of said second acoustic linear antenna.

10. The method according to claim 2, wherein the method is implemented by a device belonging to the group consisting of:
said third node; and
a centralized system.

11. A non-transitory computer-readable storage medium storing a computer program comprising a set of instructions executable by a computer to implement a method for estimating an underwater acoustic sound velocity in a network of acoustic nodes arranged along towed acoustic linear antennas and in which a plurality of acoustic signals are transmitted between the nodes, the method comprising:
obtaining two predetermined distances each separating a couple of nodes ((A,B), (B,C)) placed along a same first acoustic linear antenna;
for each couple of first and second nodes ((A,B), (B,C)), obtaining:
a first propagation duration of an acoustic signal transmitted between said first node and a third node (D) placed along a second acoustic linear antenna; and
a second propagation duration of an acoustic signal transmitted between said second node and said third node (D); and
estimating said underwater acoustic sound velocity, as a function of said two predetermined distances and said first and second propagation durations obtained for each couple of nodes.

12. A device for estimating an underwater acoustic sound velocity in a network of acoustic nodes arranged along towed acoustic linear antennas and in which a plurality of acoustic signals are transmitted between the nodes, the device comprising:
means for obtaining two predetermined distances each separating a couple of nodes placed along a same first acoustic linear antenna;
means for obtaining, for each couple of first and second nodes (A, B):
a first propagation duration of an acoustic signal transmitted between said first node (A) and a third node (D) placed along a second acoustic linear antenna ; and
a second propagation duration of an acoustic signal transmitted between said second node (B) and said third node (D); and
means for estimating said underwater acoustic sound velocity, as a function of said two predetermined distances and said first and second propagation durations obtained for each couple of nodes.

* * * * *